(12) United States Patent
Sievers et al.

(10) Patent No.: US 7,918,885 B2
(45) Date of Patent: Apr. 5, 2011

(54) VESSEL PROSTHESIS, PARTICULARLY FOR THE REPLACEMENT OF AORTA SEGMENTS NEAR THE HEART

(75) Inventors: Hans-Hinrich Sievers, Kronshagen (DE); Lisa Lippoth, Denkingen (DE)

(73) Assignee: AESCULAP AG, Tuttlingen/Donau (DE)

( * ) Notice: Subject to any disclaimer, the term of this patent is extended or adjusted under 35 U.S.C. 154(b) by 474 days.

(21) Appl. No.: 10/497,848

(22) PCT Filed: Dec. 13, 2002

(86) PCT No.: PCT/EP02/14177
§ 371 (c)(1),
(2), (4) Date: Nov. 4, 2004

(87) PCT Pub. No.: WO03/051232
PCT Pub. Date: Jun. 26, 2003

(65) Prior Publication Data
US 2005/0070994 A1    Mar. 31, 2005

(30) Foreign Application Priority Data

Dec. 14, 2001 (DE) .................................. 101 62 821
Sep. 5, 2002 (DE) .................................. 102 42 153

(51) Int. Cl.
*A61F 2/06* (2006.01)
(52) U.S. Cl. ...................... 623/1.28; 623/1.32; 623/1.49
(58) Field of Classification Search ................ 623/1.28, 623/1.29, 1.32, 1.49, 1.5–1.54
See application file for complete search history.

(56) References Cited

U.S. PATENT DOCUMENTS

| 4,544,599 | A | 10/1985 | Buttazzoni |
| 4,585,458 | A * | 4/1986 | Kurland ...................... 623/13.17 |
| 6,129,756 | A * | 10/2000 | Kugler et al. ................ 623/1.27 |
| 6,364,905 | B1 * | 4/2002 | Simpson et al. .............. 623/2.13 |
| 6,773,457 | B2 * | 8/2004 | Ivancev et al. ............... 623/1.28 |
| 6,974,471 | B2 | 12/2005 | Van Schie et al. |
| 7,189,257 | B2 | 3/2007 | Schmitt et al. |
| 2002/0156522 | A1 * | 10/2002 | Ivancev et al. ............... 623/1.13 |
| 2003/0088305 | A1 * | 5/2003 | Van Schie et al. ........... 623/1.12 |
| 2004/0019375 | A1 * | 1/2004 | Casey et al. .................. 623/1.28 |
| 2004/0210296 | A1 | 10/2004 | Schmitt et al. |

FOREIGN PATENT DOCUMENTS

AU    PR 8473    10/2001

(Continued)

OTHER PUBLICATIONS

Kazui Teruhisa, artificial Blood Vessel, machine translated version of jp-2001-161726A provided by AIPN from the JPO, published Jun. 19, 2001.*

(Continued)

*Primary Examiner* — Thomas J Sweet
*Assistant Examiner* — Matthew Schall
(74) *Attorney, Agent, or Firm* — The Nath Law Group; Tanya E. Harkins; Ari G. Zytcer (57) ABSTRACT

The invention relates to a vessel prosthesis, particularly for the replacement of aorta segments near the heart, in the form of a pleated flexible tube with folds (3), the tube being configured as an arc, and the arc shape being fixed in an extension-resistant manner, in the non-implanted state, by means of extension limiters.

10 Claims, 5 Drawing Sheets

FOREIGN PATENT DOCUMENTS

| | | |
|---|---|---|
| DE | 44 30 485 | 3/1996 |
| DE | 101 62 821 | 6/2003 |
| EP | 1245202 A1 * | 10/2002 |
| JP | 11-332892 A | 12/1999 |
| JP | 2001-161726 A | 6/2001 |
| JP | 2001161726 | 6/2001 |
| WO | 99/11198 A1 | 3/1999 |
| WO | WO 03/034948 A1 | 5/2003 |
| WO | 03/051232 A1 | 6/2003 |

OTHER PUBLICATIONS

Office Action issued in the counterpart German Patent Application, Jul. 5, 2010, two (2) pages.

* cited by examiner

VESSEL PROSTHESIS, PARTICULARLY FOR THE REPLACEMENT OF AORTA SEGMENTS NEAR THE HEART

The invention relates to a vessel prosthesis, particularly for the replacement of aorta segments near the heart.

Vessel prostheses for the replacement of hollow organs in humans and animals, in particular of blood vessels, have been known for a long time. They can be made of textile material (DE-A2 26 13 575, DE-A2 20 09 349, DE-A1 24 61 370) and of non-textile material (cf. EP-A1 0 106 496, GB-A1 15 06 432).

Since the blood vessels, in particular the larger ones, have, along most of their length, an approximately straight course through the body, the vessel prostheses also generally have the shape of straight tubes.

However, there are also vessels or vessel sections which have a curved course. Thus, for example, the aorta in humans has an arched course in the thoracic region just after the exit from the heart. In this region it is divided into the following sections: The aorta originates from the left ventricle with the first, ascending section (pars ascendens). This part merges into the aortic arch (arcus aortae), which in turn merges into the descending part of the aorta (pars descendens). All three sections have a more or less curved course, in particular the pars ascendens and, most of all, the aortic arch. The pars descendens is curved in particular at its start.

In the event of diseases, such as arteriosclerosis, or injuries in the region of said curved aorta sections, heart surgery has hitherto often involved the use of straight vessel prostheses which are brought to the desired arched shape by the operating surgeon during the operation itself. This has serious disadvantages for the operating surgeon and in particular for the patient. On the one hand, it is awkward for an operating surgeon to bring a straight vessel prosthesis to the desired arched shape during the operation and then to sew it on to the natural vessel ends. Much more serious, however, are the disadvantages for the patient, since these prostheses exhibit buckling in the implanted state. This buckling occurs because the artificial aortic arch lengthens upward, in the event of an internal pressure, and as a result loses its arc shape.

This buckling can form eddies, reduce the cross section of flow, and possibly promote clots and thromboembolism. It therefore represents a not inconsiderable danger to the patients.

It is possible to produce pre-curved vessel prostheses from a textile tube material with pleats. To do so, straight sections can be drawn onto a U shape and thermally fixed. These thermally pre-formed vessel arches have the advantage that they are easier for an operating surgeon to handle and to implant compared to the aforementioned straight vessel prostheses which have to be brought to the appropriate shape during the operation itself. However, these thermally fixed vessel arches, in the implanted state, exhibit similar buckling to that observed also in the straight vessel prostheses.

From the monograph entitled Ischemic Heart Disease, 1999, page 398, Mosby/London, ISBN 0723429111, a vessel prosthesis is also known which, for fixing the arc shape, has on the inner side a row of individual stitches which provide for a partial gathering-together of the wall of the vessel prosthesis on the inner side of the arc. The thread ends of the individual stitches are each knotted to one another. However, this vessel arch too has weaknesses due to shape changes in the implanted state.

It is therefore an object of the invention to make available a vessel prosthesis which avoids the aforementioned shape changes, in particular buckling, and, in the implanted state, even in the event of internal pressure, substantially maintains the full cross section of flow.

The object is achieved by a vessel prosthesis, in particular for the replacement of aorta segments near the heart, in the form of a pleated flexible tube with folds, the tube being configured as an arc, and the arc shape being fixed in an extension-resistant manner, in the non-implanted state, by means of at least one continuous extension limiter running in the longitudinal direction of the vessel prosthesis and/or by a multiplicity of extension limiters running in the transverse direction. The folds of the pleating are gathered together to fix the arc. The gather preferably extends over a part of the tube circumference amounting to 10 to 180°, in particular 15 to 90°.

In contrast to the aforementioned pre-formed vessel arches which are only thermally fixed and which, in the non-implanted state, can be brought into a straight shape by pulling them, this is not possible in the vessel prosthesis according to the invention.

A comparison between the known vessel prosthesis having individual stitches at the inner side of the arc and the vessel prosthesis according to the invention shows that the vessel prosthesis according to the invention is also much more shape-stable than this known vessel prosthesis. The extension-resistant fixing, preferably provided or configured on the inner side of the arc, affords, in the implanted state, a high degree of shape stability, particularly in cross section. By gathering together the folds of the pleat for fixing the arc over a part of the tube circumference, there is a marked increase in the stability of the arc shape. This in turn means that, in the implanted state, there is a high degree of shape stability, particularly in cross section. In contrast to the above-described vessel prostheses of the prior art, there is no twisting or widening of the arc, thus also avoiding the development of buckling.

In a particularly preferred embodiment of the vessel prosthesis according to the invention, the tube is configured as a thermally pre-fixed arc. This additional thermal pre-fixing ensures a further increase in the stability of the arc shape. In addition, the gathering-together is easier to do on a thermally pre-fixed arc.

It is preferable for the vessel prosthesis according to the invention to have a porous wall because this promotes the ingrowth of tissue and small blood vessels. It is particularly preferable that the vessel prosthesis is made of textile material and is in particular knitted or woven. It is particularly preferable that the vessel prosthesis, particularly on the outside wall, is coated with a natural or synthetic absorbable material. A suitable example is gelatin, in particular cross-linked gelatin. This material is slowly absorbed after implantation and replaced by endogenous tissue.

The vessel prosthesis according to the invention has, at least in the arched area, a fold-type pleating in the prosthesis wall. The pleating can be configured as a coil shape or as closed rings. Generally, pleating gives the vessel prosthesis elasticity and diameter stability.

The vessel prosthesis advantageously has 3 to 12, preferably 4 to 8, in particular 6, folds per cm of prosthesis length. The folds of the pleating advantageously have a depth of 0.5 to 2.5 mm, preferably 1 to 1.5 mm, which particularly in prostheses of greater diameter is greater than in prostheses of smaller diameter. In general, the fold depth is at least 1 mm.

Starting from their peak, the folds on the outer side of the arc advantageously enclose an angle of 70° to 110°, in particular of ca. 90°.

To achieve the aforementioned extension-resistant fixing of the arc, the folds of the pleating are preferably fixed in a position close to one another at least on the inner side of the arc. To achieve stability against twisting of the vessel prosthesis, the latter can also have a lateral fixing of the folds of the pleating. The fold spacings are advantageously narrowest on the inner side of the arc and widen in the direction of the sides of the arc. The folds of the pleating on the inner side of the arc are preferably so brought close together that they bear on one another on the inner side of the arc.

In a particularly preferred embodiment of the vessel prosthesis according to the invention, the folds of the pleating for forming and fixing an arc are permanently gathered together, in particular sewn together, over a part of the tube circumference which amounts to 10 to 180°, in particular 15 to 90°, along the tube circumference. The extent of the curvature is determined by the number of seams and the stitch spacing. Each fold of the pleating is preferably connected, in particular sewn, to the next one, which ensures a high degree of shape stability. Each seam preferably comprises a multiplicity of stitches.

In a particularly preferred variant of the vessel prosthesis according to the invention, it has, as fixing means, at least one seam consisting of at least one thread, said seam having at least four, preferably at least eight, through-runs of the prosthesis wall. For fixing the arc, the folds of the pleating are brought close together, in particular so as to touch each other, at least over a part of the tube circumference. In the present description, a seam is defined as one which has at least eight through-runs and is formed from a continuous thread with thread start and thread end. In this connection, a through-run is understood as a site where the sewing thread passes through the prosthesis wall. Thread start and thread end are preferably spatially separate from one another. A seam can have one stitch, several stitches or a multiplicity of stitches, for example cross-stitches and/or ride-over stitches.

In one embodiment of the invention, the vessel prosthesis according to the invention has at least one seam having a multiplicity of through-runs, in particular ca. 20 to 250 through-runs, the seam running preferably in the longitudinal direction and/or circumferential direction of the prosthesis. If the seam runs in the longitudinal direction of the prosthesis, just one seam is enough to achieve a sufficiently high degree of shape stability. By means of the multiplicity of continuous through-runs, a high degree of shape stability is achieved. Advantageously, the vessel prosthesis according to the invention is made extension-resistant at least on the inner side of the arc. Fixing over a circumference width of 10° gives good results already. Fixing over a width of 15° to 30° of the tube circumference affords increased shape stability. To achieve the abovementioned extension-resistant fixing of the arc, the folds of the pleating are fixed in a position close to one another at least on the inner side of the arc. If only one seam is provided, this preferably has a width of at 10° of the arc circumference. To achieve a further stability against twisting of the vessel prosthesis, the latter can also have lateral fixing of the folds of the pleating. The seams can run in the longitudinal direction and/or transverse direction of the prosthesis. For this purpose, it is possible to provide widened seams or a number of parallel seams. The fold spacings are preferably narrowest on the inner side of the arc and widen in the direction of the sides of the arc. The folds of the pleating on the inner side of the arc are preferably brought so close together that they at least partially bear on one another on the inner side of the arc.

In one embodiment of the prosthesis according to the invention, at least one continuous longitudinal seam is provided, in particular on a central line of the inner side of the arc, in which case the thread runs over a multiplicity of stitches from one end of the gather to the other. In this way, all the folds are gathered together along one line, i.e. the folds are gathered together without leaving a gap. As has already been mentioned, this is not the case in the vessel prostheses of the prior art. Intermediate ties, in particular intermediate knots, between the folds allow the prosthesis to be shortened or individual stitches to be removed, without the whole seam coming unstitched.

In a preferred variant of the vessel prosthesis according to the invention, at least one seam has cross-stitches, and in particular consists of such. The stitches can be single, double or multiple cross-stitches. A seam, in particular a longitudinal seam, advantageously has between ca. 10 and 40, preferably between 20 and 30, stitches, preferably cross-stitches, per seam. Transverse seams are in general shorter, since they cover at most 180° of the prosthesis circumference. Their stitch count is ca. 10 to 20. Cross-stitches have both a longitudinal extent and also a transverse extent.

It is particularly preferable that seams, in particular seams having cross-stitches, run in the circumferential direction of the prosthesis, in this case with preferably numerous parallel seams running in the circumferential direction. They can extend over a width of the prosthesis which corresponds to ca. 5 to 50%, in particular ca. 10 to 40%, of the total circumference of the tube. The seams running in the circumferential direction can be connected to one another by a continuous thread to form a continuous seam. Therefore, seams with cross-stitches can run in the longitudinal direction and/or circumferential direction. This course of the seams in the circumferential direction of the prosthesis provides for considerable widening of the fixing, and the degree of gathering-together of the folds is also increased. Compared to a vessel prosthesis in which only individual points on the inner side of the prosthesis are gathered together, this provides for a planar, in particular continuous course of the gathered areas. This affords a substantial increase in shape stability.

In a further embodiment of the prosthesis according to the invention, at least one seam has ride-over stitches, and in particular consists of such. The seams, in particular the seams consisting of ride-over stitches, preferably run in the circumferential direction of the prosthesis. Several seams, preferably parallel to one another, can be arranged running in the circumferential direction. These seams can either be free or connected to one another. It is also possible to arrange several seams with smaller stitch count one behind the other in the circumferential direction. In a particularly preferred embodiment, seams with small stitch counts are arranged both behind one another and also alongside one another, running in the circumferential direction. The seams arranged alongside one another preferably have an identical stitch count. This stitch count can be between 1 and 10, preferably between 1 and 3.

In a further preferred embodiment, at least one seam has only through-stitches, and in particular consists exclusively of such. This seam variant is very easy to produce. The seam has at least eight, particularly preferably more than eight, through-runs. In the case where there are more than eight through-runs, the threads can be individually tied, in particular knotted, between individual through-runs. At least one seam advantageously has at least one thread which passes through the folds of the pleating and runs the entire length of the gather. The thread ends are preferably tied off, in particular knotted, individually. The thread advantageously has ties between the thread ends, in particular every 1-2 pleat folds. Such a seam has the advantage that it is very easy to produce.

The thread ends of a seam are advantageously arranged at a distance from one another. The individual thread ends are preferably tied off individually, in particular knotted.

In a particularly preferred variant of the vessel prosthesis according to the invention, the longitudinal seams have, between the thread ends, in particular every 2-3 pleat folds, ties, in particular knots, which are preferably free of thread ends. These ties have the great advantage that, despite continuous thread, the whole seam does not come unstitched if the thread is cut through, for example during cutting of the vessel prosthesis to size by the operating surgeon. The thread can detach from the vessel prosthesis from the place where it is cut through to, at the very most, the next tie. The ties preferably lie between the stitches. It is particularly preferable for each stitch to be followed by a tie.

Advantageously, two to six, in particular two to three, folds are gathered together in particular by a transverse seam.

In a preferred embodiment of the vessel prosthesis according to the invention, it has several, in particular two, longitudinal seams which are preferably substantially parallel and run across a multiplicity of pleat folds. As in the abovementioned embodiment in which the stitches run in the circumferential direction of the prosthesis, this permits gathering-together of the folds of the pleating over a greater area in the circumferential direction. The parallel seams are preferably arranged axially symmetrical to a line running in the center of the inside of the arc. Longitudinal seams can be combined with seams in the circumferential direction of the prosthesis.

It is particularly preferable that the seams on the inner wall of the prosthesis do not lie substantially open, in particular the inner edges of the pleating folds are free from thread material. The seams preferably run only through the walls of the pleating and if appropriate over the outer edges thereof. In this way, the seams have only very slight contact with blood, which for example reduces the risk of thrombosis.

In a further embodiment of the vessel prosthesis, the folds of the pleating, for fixing the arc, are fixed in a position close to one another on the inner side of the arc by at least one strip, in particular made of plastic, secured thereon. It is also possible that such strips are also applied at the sides in order to achieve stability against twisting. Said strips are advantageously applied at least partially, in particular only, on the outside edges of the folds or the fold peaks. This means in turn that tissue and small blood vessels can easily grow into the fold valleys, since at these places the pores are not covered by the strip. In a preferred embodiment, said strips are adhesively bonded and/or sewn onto the vessel prosthesis.

In addition to the abovementioned preferred embodiments in which the folds of the pleating are fixed in a position close to one another on the inner side of the arc by being sewn together or by means of a strip being adhesively bonded or sewn on, it is also possible for the folds of the pleating to be fixed close together on the inner side of the arc also by shrinking. For this purpose, it is possible to at least partially incorporate a high-shrinkage material, in particular a high-shrinkage yarn, into the wall of the vessel prosthesis.

The vessel prostheses according to the invention preferably have a diameter of 15 to 50 mm, in particular 20 to 40 mm. The diameter is generally chosen so that it corresponds to the natural diameter of the replaced vessel. It is also possible for a vessel prosthesis according to the invention to be fitted in a person who is still growing, in which case, however, the vessel prosthesis will have to be changed from time to time in order to adapt the diameter to the increasing diameter of the growing vessel.

The radius of the vessel arc in the longitudinal center axis of the prosthesis is advantageously 3 to 6 cm, in particular 4 to 5 cm. These values too depend on the anatomical circumstances of the patient.

Generally, the curve of the arc is adjoined at at least one end of the vessel prosthesis according to the invention, preferably at both ends, by a straight prosthesis portion. In the case of the aorta prosthesis, these straight portions correspond to at least parts of the pars ascendens and/or pars descendens. These straight portions can also be unpleated.

The arc of the prosthesis advantageously encloses an angle of 120 to 330, in particular 180 to 270°. The vessel prosthesis according to the invention preferably has a conicity corresponding substantially to the conicity of the natural aorta.

All the larger blood vessels in the human body have branches. Thus, three blood vessels branch off from the aorta in the area of the aortic arch (the brachiocephalic trunk and the left common carotid and left subclavian arteries). To take account of these natural circumstances, a preferred embodiment of the vessel prosthesis according to the invention has artificial branches leading off from the vessel prosthesis and corresponding to said branching vessels. Depending on requirements, and on anatomical circumstances, they can have different diameters and lengths. The length of these portions branching off from the prosthesis depends in particular on the extent of the disease or injury of the affected vessels.

For example, if only the aortic arch is affected by disease or injury, then it is also possible for the natural vessel branches to be sewn directly onto openings in the vessel prosthesis, and the vessel prosthesis has no artificial branches. Said openings could either be already provided in the prosthesis or could be cut out from the prosthesis wall by the surgeon during the operation itself.

In addition, the prosthesis can also be equipped with an attachment for reperfusion by means of the heart-lung machine.

The vessel prosthesis according to the invention can also have bifurcations (branches) and bulbi (widened areas).

Further details and features of the invention are set out in the following description of a preferred illustrative embodiment in conjunction with the subclaims. The respective features can be realized in isolation or in combinations with one another.

Figure 1:
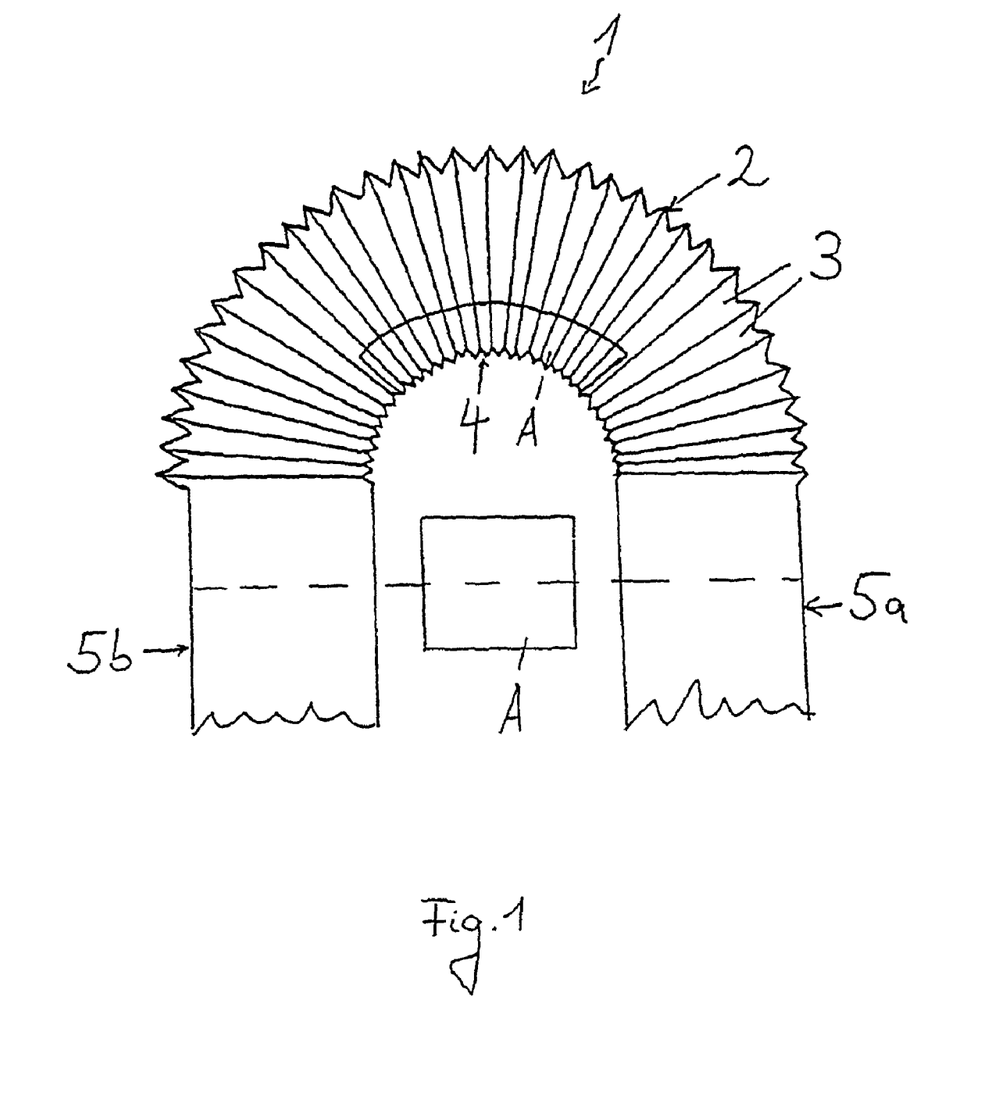
FIG. 1: side view of a vessel prosthesis according to the invention made of textile material, with sewn fixing.

FIG. 1 shows an arc-shaped vessel prosthesis 1 according to the invention made of a textile material, with sewn fixing. A multiplicity of different seams are involved here. These are shown diagrammatically in FIGS. 1A to 1E. This prosthesis is suitable for replacement of arcuate vessels or vessel sections, in particular for the replacement of the aortic arch and parts of the pars ascendens and pars descendens. The arc of the tubular vessel prosthesis encloses an angle of 180°. The prosthesis has a circumference of ca. 7 cm. Only the peaks of the folds can be seen in FIGS. 1A to 1D.

In the area of the arched section 2 of the illustrated vessel prosthesis, the latter has a fold-type pleating in the prosthesis wall, the folds 3 of this pleating being configured as closed rings. The folds 3 of the pleating are fixed in a position close to one another on the inner side 4 of the arc for fixing the arc. In the present illustrative embodiment, this fixing is achieved by sewing together the folds over a part of the tube circumference along the inner side of the arc. Details of alternative seams are given in the descriptions of FIGS. 1a to 1e. The fold spacings are narrowest on the inner side 4 of the arc and widen in the direction of the outer side of the aortic arch 2. Adjoining the arched and pleated section 2 of the vessel prosthesis 1 at both ends, there are a straight portion 5a and a straight portion 5b. These straight portions 5 have no pleating.

Figure 1A:
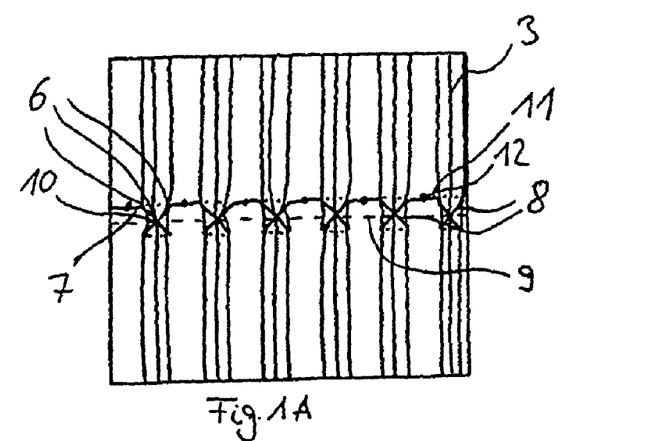
FIG. 1a: plan view of a cutout A from the central area of the crown of the arc of a vessel prosthesis according to the invention, with a seam consisting of individual cross-stitches.

FIG. 1A shows a cutout A from the central area of the inner crown of the arc of a vessel prosthesis according to the invention. This vessel prosthesis has a seam 7 which runs in the longitudinal direction and which has a multiplicity of individual cross-stitches 8. The course of this seam is such that an imaginary center line 9 of the inner side of the arc extends substantially through the intersection points 10 of the individual cross-stitches. The seam 7 has a base line 11 which connects the stitches 8 and along which the thread material extends along the entire gather of the pleating and connects the cross-stitches to one another and holds them on one another. The seam 7 additionally has intermediate ties of the thread in the form of knots 12 which lie on the base line. A knot follows after each stitch. The vessel prosthesis has ca. 3 stitches per cm. In total, there are 23 stitches provided along the length of the arc. Three folds of the pleating 3 are gathered together by each stitch. Thus, each stitch comprises at least 12 through-runs (per fold 4 through-runs of the prosthesis wall). The folds are gathered together over a part of the tube circumference which amounts to ca. 15°. The whole seam consists of a continuous thread.

Figure 1B:
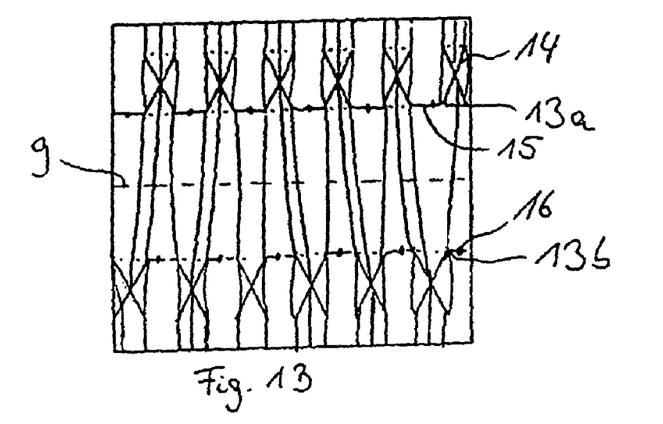
FIG. 1b: plan view of a cutout from the central area of the crown of the arc of a vessel prosthesis according to the invention, with two parallel seams consisting of individual cross-stitches.

FIG. 1B shows a cutout from the central area of the inner crown 9 of the arc of a vessel prosthesis according to the invention. In this embodiment, two seams 13a, 13b run substantially parallel in the longitudinal direction. The two seams have cross-stitches 14 which are connected to one another by a base line 15 of thread material which holds the individual stitches on one another and thus likewise contributes to the gather. The thread material on the base line has knots 16, with a knot following after each stitch. The stitches run ca. 6 mm in the circumferential direction of the prosthesis. The two seams are arranged approximately axially symmetrically parallel to the line 9. Each seam has between 20 and 25 stitches. Each seam 13a and 13b has ca. 3 to 4 cross-stitches per cm of prosthesis length. Either two or three folds of the pleating are gathered together per cross-stitch. As in FIG. 1a, each stitch comprises at least 12 through-runs. The stitches of the two seams do not lie directly opposite one another, but are in each case offset relative to one another by one pleat fold. About 90° of the tube circumference is included by the outer edge of the first seam and the outer edge of the second seam. Between the two seams, in the inner area of the arc, the folds bear close on one another.

Figure 1C:
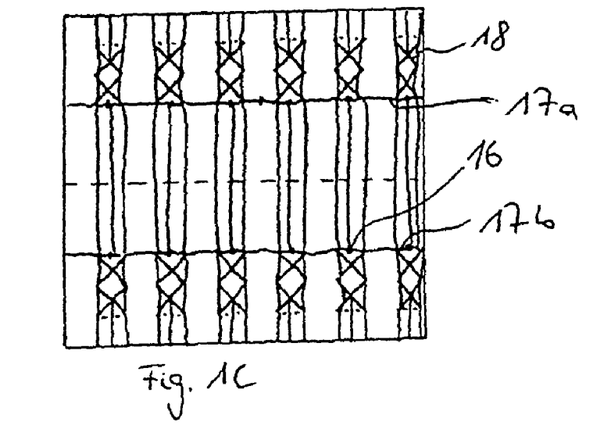
FIG. 1c: plan view of a cutout from the central area of the crown of the arc of a vessel prosthesis according to the invention, with two parallel seams consisting of double cross-stitches.

FIG. 1C shows a cutout from the central area of the crown of the arc of a vessel prosthesis according to the invention. This embodiment has, like the embodiment in FIG. 1b, two parallel seams 17a and 17b running in the longitudinal direction. The embodiment in FIG. 1C is identical to the embodiment in FIG. 1B, with the following exceptions: The stitches are double cross-stitches 18; the stitches of the two seams lie opposite one another, as a result of which the stitches lying opposite one another gather together the same folds (in the inner side of the arc in each case 3 folds, and in the outer area at the arc ends in each case 2 folds); the knots lie for the most part in the area of the stitches. Each double cross-stitch, which gathers together 3 folds, comprises 16 through-runs (6 through-runs each of the two outer folds, and 4 through-runs of the middle fold). Each double cross-stitch, which gathers together 2 folds, comprises at least 18 through-runs.

Figure 1D:
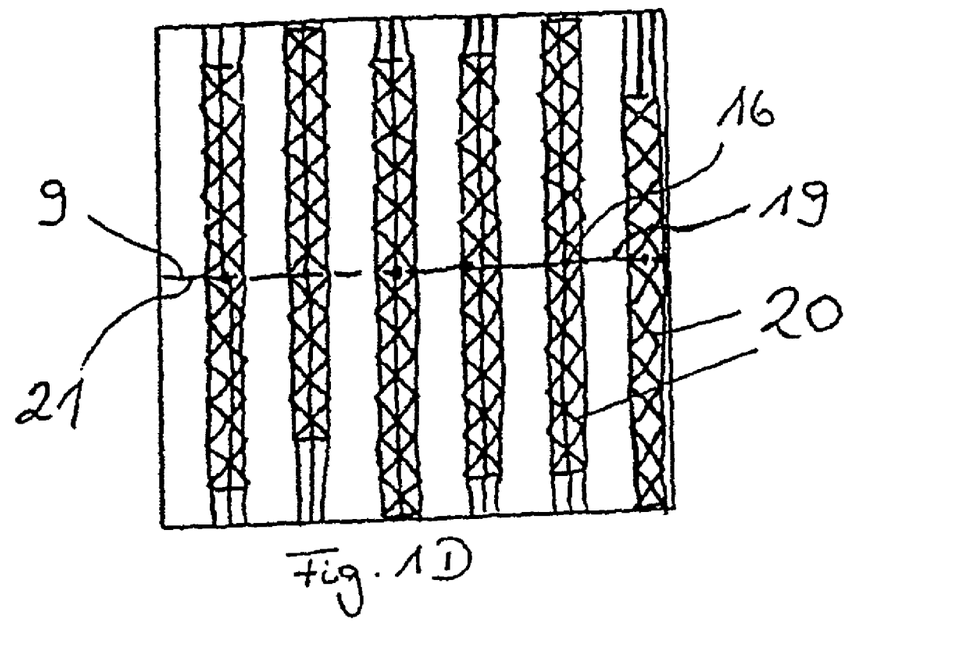
FIG. 1d: plan view of a cutout from the central area of the crown of the arc of a vessel prosthesis according to the invention, with a seam consisting of multiple cross-stitches.

FIG. 1D shows a cutout from the central area of the crown of the arc of a vessel prosthesis according to the invention. This embodiment has a seam 19 which has numerous parallel multiple cross-stitches 20. These multiple cross-stitches have a different number of individual cross-stitches. This number ranges between 11 and 16 stitches. The multiple cross-stitches protrude right and left beyond the base line 21 and run in the circumferential direction of the vessel prosthesis. In doing so, they gather together the folds of the pleating over a part of the tube circumference amounting to between 100 and 160°. Extending on the base line, approximately in the central line 9, there is a thread which connects the individual transverse seams to one another and in each case is a part of the continuous thread material forming the seams. By means of the longitudinal connection of the individual transverse seams, the overall combination of the seams is given a planar character. Per multiple cross-stitch, 3 folds per stitch are gathered together in the central area of the arc (crown area), and, in the outside areas of the arc 2, folds are gathered together per multiple cross-stitch. The individual multiple cross-stitches run approximately parallel to one another. The present embodiment has 24 multiple cross-stitches and has ca. 4 multiple cross-stitches per cm of prosthesis length. This embodiment also has knots 16 which are located substantially in the area of the multiple cross-stitches. There are at least as many intermediate knots as there are multiple cross-stitches.

Figure 1E:
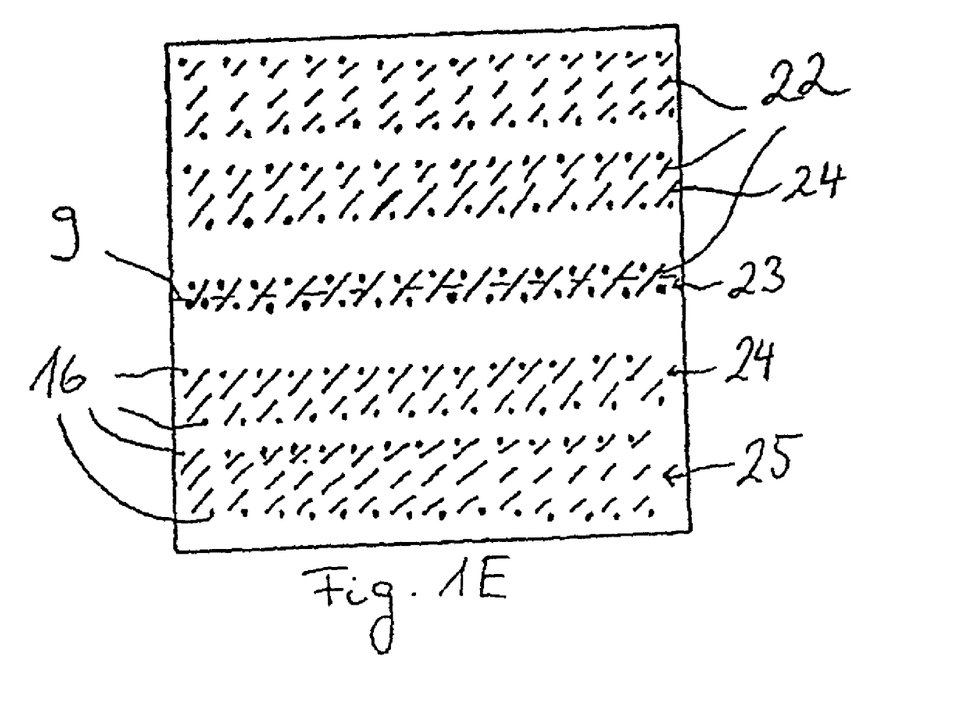
FIG. 1e: plan view of a cutout from the central area of the crown of the arc of a vessel prosthesis according to the invention, with a multiplicity of seams consisting of ride-over stitches.

FIG. 1E shows a cutout from the central area of the crown of the arc of a vessel prosthesis according to the invention. In contrast to the previously described embodiments, several parallel seams run in the longitudinal direction of the prosthesis, namely one along the inner crown 9 and in each case two seams to the right and two to the left thereof. The longitudinal seams have a width of at least two, preferably two to four, stitches and are divided in the longitudinal direction into a multiplicity of individual transverse seams arranged in rows. The seams of this embodiment have ride-over stitches 22. The threads of the individual seams have knots 16 at their ends. Along the central mid-line 9 there is a row of individual seams 23 with single ride-over stitches. These individual seams 23 are not connected to one another. In both directions in the circumferential direction of the vessel prosthesis, each individual seam 23 with single ride-over stitch is followed, at a distance of ca. 4 mm, in each case by a seam 24 consisting of two ride-over stitches. These individual seams run in the circumferential direction of the vessel prosthesis. The individual seams 23 and the seams 24 with two ride-over stitches are located in rows along the prosthesis. The threads of said individual seams 24 have knots 16 at their ends. These seams 24 with two ride-over stitches are followed, in the circumferential direction and at a distance of ca. 7 mm, by further individual seams 25 which all have three ride-over stitches. The threads of these individual seams too have knots 16 at their ends. The individual seams 25 lie approximately on a line in the circumferential direction, with in each case an individual seam 24 with two ride-over stitches and one seam 23 with a single ride-over stitch. Therefore, five seams lie substantially one behind the other in the circumferential direction (two seams with three ride-over stitches, two seams with two ride-over stitches, and one seam with single ride-over stitch). The individual seams 25 also lie in longitudinal rows. By the individual seams lying behind one another on lines in the circumferential direction and in rows in the longitudinal direction, the folds of the pleat are gathered together flat. Seams with single ride-over stitches comprise 8 through-runs, seams with two ride-over stitches comprise 12 through-runs, and seams with three ride-over stitches comprise 16 through-runs. For the sake of clarity, the folds are not shown in the present figure. Here, the folds of the pleating for fixing the arc are gathered together over a part of the tube circumference amounting approximately to 180°. This embodiment has, in the longitudinal direction, ca. 30 single ride-over stitches and thus ca. 60 seams with two ride-over stitches (in each case 30 alongside one another in the longitudinal direction) and ca. 60 seams with three ride-over stitches.

Figure 2:
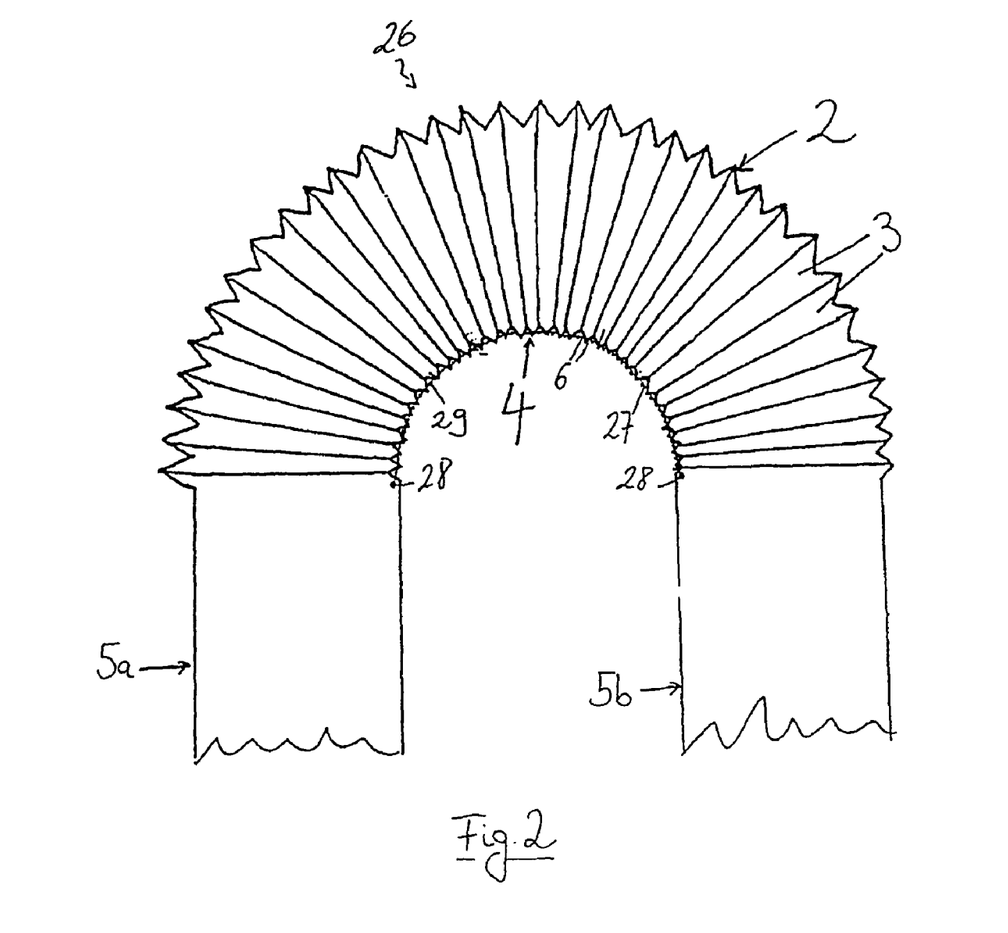
FIG. 2: enlarged side view of a vessel prosthesis according to the invention, with sewn fixing.

FIG. 2 also shows a vessel prosthesis 26 according to the invention made of a textile material with sewn fixing. The seam in this case involves a variant type which is very easy to produce. This seam has a continuous thread 27 running centrally in the longitudinal direction and passing through the folds 3 of the pleat. The thread 27 has ties 28, e.g. knots, at its ends. These ties 28, on the one hand, permit gathering on the inner side 4 of the arc, and, on the other hand, said ties permit fixing of the thread 27 in the prosthesis 26. The seam comprises two through-runs 6 per fold. The seam, which is a longitudinal seam, also has ties 29, in particular knots, between the thread ends. These knots are located in each fold 3 of the pleating. As in the variants already described above, these knots 29 prevent unraveling of the seam in the event of the latter possibly being cut through.

Said ties (knots) 29 can also be somewhat less numerous and, for example, can be present only in every second or third fold. As has already been mentioned above, the main advantage of this seam is that it is easy to produce. Several such seams can also lie parallel alongside on another.

This embodiment too has an arched part 2 with pleating, both ends of the arc being adjoined, respectively, by straight, unpleated sections 5a and 5b.

Figure 3:
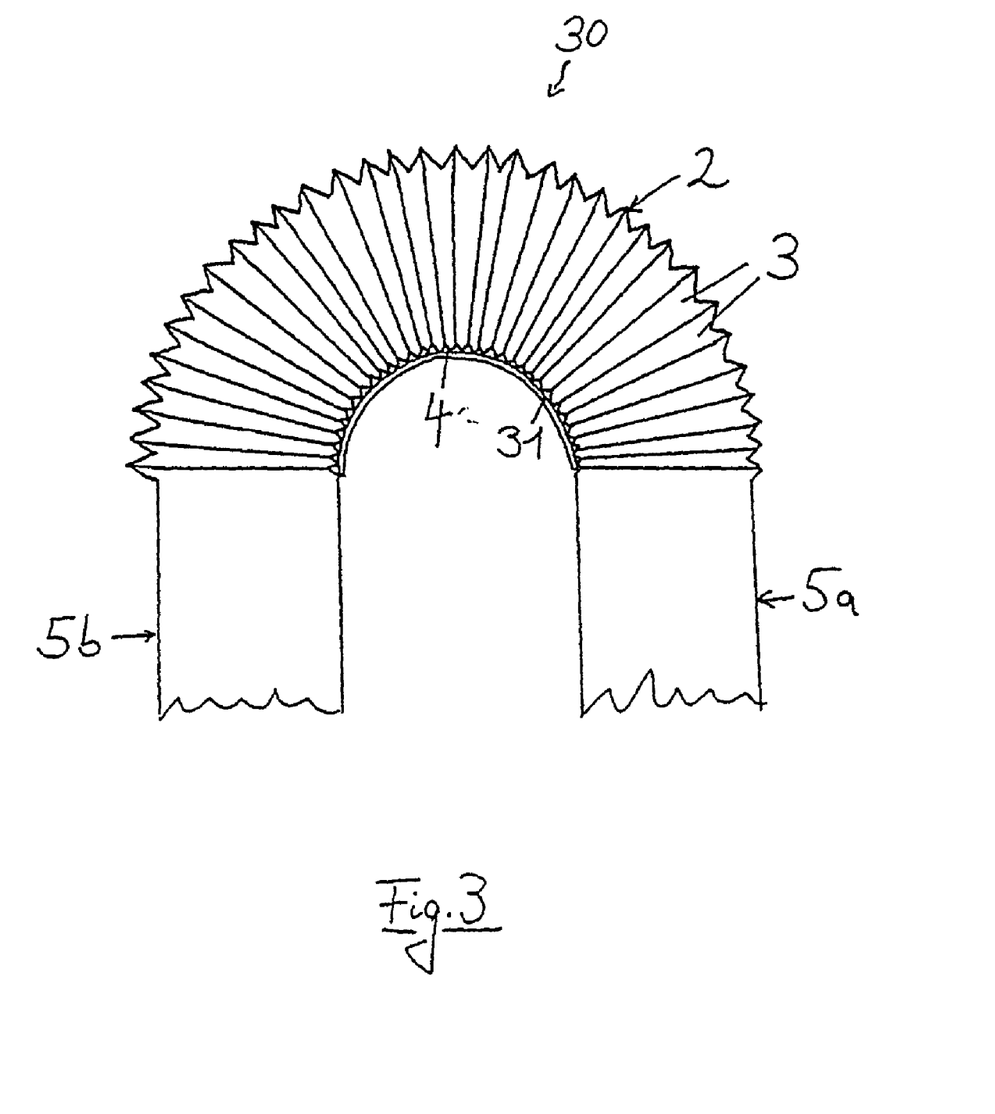
FIG. 3: side view of a vessel prosthesis according to the invention made of textile material, with fixing by means of a glued-on plastic strip.

FIG. 3 shows a vessel prosthesis 30 according to the invention, likewise made of a textile material. This prosthesis too is suitable for the use of arched prostheses or vessel portions, in particular for the replacement of the aortic arch and areas of the pars ascendens and pars descendens. The arc of the vessel prosthesis shown encloses an angle of 180°. In the area of the arched portion 2 of the vessel prosthesis shown, the latter has a fold-type pleating in the prosthesis wall, the folds 3 of this pleating being configured as closed rings. The folds 3 of the pleating are fixed in a position close to one another on the inner side 4 of the arc for fixing the arc. In the present illustrative embodiment, this fixing is obtained by an extension-resistant plastic strip 31 bonded adhesively onto the fold peaks of the inner side of the arc. The fold spacings on the inner side 4 of the arc are narrowest and they widen in the direction of the outer side of the aortic arch. Analogously to the illustrative embodiment in FIG. 1, the arched and pleated portion 2 of the vessel prosthesis 7 is adjoined at both ends of the arc by, respectively, straight portions 5a and 5b. These straight portions 5a and 5b have no pleating.

Tests comparing the vessel prostheses according to the invention with vessel prostheses from the prior art have shown that, when the internal pressure increases, the shape of the vessel prostheses according to the invention remains stable. By contrast, in vessel prostheses from the prior art, it has been observed that, when the internal pressure increases, these substantially deform and exhibit buckling.

The invention claimed is:

1. A vessel prosthesis for the replacement of aorta segments near the heart comprising a pleated flexible tube with folds,
   the tube being configured as a thermally pre-fixed arc
   the arc shape being fixed in an extension-resistant manner, in the non-implanted state, by means of at least one continuous extension limiter running in the longitudinal direction and/or a multiplicity of extension limiters running in the transverse direction, and
   the folds of the pleating being gathered together to fix the arc,
   wherein the prosthesis has, as an extension limiter, at least one seam with at least eight through-runs, the at least one seam running in the longitudinal direction and/or in the circumferential direction of the prosthesis, and
   wherein thread ends are arranged at a distance from one another and longitudinal seams have, between the thread ends, intermediate ties.

2. The vessel prosthesis as claimed in claim 1, wherein folds of the gathered pleating extend over a part of the tube circumference amounting to 10 to 180°.

3. The vessel prosthesis as claimed in claim 1, wherein at least one seam is located on a central line of the inner side of the arc.

4. The vessel prosthesis as claimed in claim 1, wherein at least one seam has cross-stitches.

5. The vessel prosthesis as claimed in claim 1, wherein at least one seam has between ca. 10 and 40 stitches per seam.

6. The vessel prosthesis as claimed in claim 1, wherein at least one seam has through-stitches.

7. The vessel prosthesis as claimed in claim 1, wherein at least one seam has at least one thread which passes through the folds of the pleating and runs an entire length of a gather.

8. The vessel prosthesis as claimed in claim 1, wherein the thread ends are tied off individually.

9. The vessel prosthesis as claimed in claim 1, wherein in each case 2 to 6 folds are gathered together by a transverse seam.

10. The vessel prosthesis as claimed in claim 1, wherein it has several longitudinal seams which run across a multiplicity of pleat folds.

\* \* \* \* \*